(12) United States Patent
Drake et al.

(10) Patent No.: US 10,394,324 B2
(45) Date of Patent: Aug. 27, 2019

(54) CONFIGURATION FOR ADJUSTING A USER EXPERIENCE BASED ON A BIOLOGICAL RESPONSE

(71) Applicant: Disney Enterprises, Inc., Burbank, CA (US)

(72) Inventors: Edward Drake, Stevenson Ranch, CA (US); Benjamin F. Havey, Burbank, CA (US); Mark Arana, West Hills, CA (US); Alexander Chen, La Canada Flintridge, CA (US)

(73) Assignee: Disney Enterprises, Inc., Burbank, CA (US)

( * ) Notice: Subject to any disclaimer, the term of this patent is extended or adjusted under 35 U.S.C. 154(b) by 0 days.

(21) Appl. No.: 15/457,274

(22) Filed: Mar. 13, 2017

(65) Prior Publication Data

US 2018/0260026 A1 Sep. 13, 2018

(51) Int. Cl.
*G06F 3/01* (2006.01)
*A61B 5/16* (2006.01)
(Continued)

(52) U.S. Cl.
CPC .............. *G06F 3/015* (2013.01); *A61B 5/165* (2013.01); *A61M 21/02* (2013.01); *G06F 3/016* (2013.01); *A61B 5/01* (2013.01); *A61B 5/021* (2013.01); *A61B 5/024* (2013.01); *A61B 5/0476* (2013.01); *A61B 5/0533* (2013.01); *A61B 5/163* (2017.08);
(Continued)

(58) Field of Classification Search
CPC ........ G06F 3/015; G06F 3/016; G06F 19/322; A61B 5/165; A61B 5/01; A61B 5/021; A61B 5/0476; A61B 5/0533; A61B 5/163; A61M 21/02; A61M 2021/0027; A61M 2021/005; A61M 2205/3303; A61M 2205/3313; A61M 2230/04; A61M 2230/10; A61M 2230/50; A61M 2230/65; G16H 10/60
See application file for complete search history.

(56) References Cited

U.S. PATENT DOCUMENTS 7,654,901 B2    2/2010  Breving
8,308,562 B2   11/2012  Patton
(Continued)

OTHER PUBLICATIONS

Negini, Faham, "Play Experience Enhancement Using Emotional Feedback," A Thesis Submitted to the College of Graduate Studies and Research, Department of Computer Science, University of Saskatchewan, Saskatoon, http://citeseerx.ist.psu.edu/viewdoc/download?doi=10.1.1.883.5546&rep=rep1&type=pdf, 2014.
(Continued)

*Primary Examiner* — Stephen G Sherman
(74) *Attorney, Agent, or Firm* — Patent Ingenuity, P.C.; Samuel K. Simpson

(57) ABSTRACT

An apparatus has a receiver that receives a biological response of a user to an event that occurs during a user experience. Further, the apparatus has a memory that stores one or more predefined criteria that indicate an expected biological response to the event. In addition, the apparatus has a processor that compares the biological response to the one or more predefined criteria and adjusts the user experience based at least upon the biological response failing to meet the one or more predefined criteria.

17 Claims, 6 Drawing Sheets

(51) Int. Cl.
*A61M 21/02* (2006.01)
*A61M 21/00* (2006.01)
*G16H 10/60* (2018.01)
*A61B 5/01* (2006.01)
*A61B 5/021* (2006.01)
*A61B 5/024* (2006.01)
*A61B 5/0476* (2006.01)
*A61B 5/053* (2006.01)

(52) U.S. Cl.
CPC ............... *A61M 2021/005* (2013.01); *A61M 2021/0027* (2013.01); *A61M 2205/3303* (2013.01); *A61M 2205/3313* (2013.01); *A61M 2230/04* (2013.01); *A61M 2230/10* (2013.01); *A61M 2230/50* (2013.01); *A61M 2230/65* (2013.01); *G16H 10/60* (2018.01)

(56) References Cited

U.S. PATENT DOCUMENTS

| | | | |
|---|---|---|---|
| 9,132,342 | B2 | 9/2015 | Balachandreswaran et al. |
| 9,179,855 | B2 | 11/2015 | Burdea et al. |
| 9,498,705 | B2 | 11/2016 | May et al. |
| 9,511,289 | B2 | 12/2016 | Bond et al. |
| 9,545,567 | B2 | 1/2017 | Han et al. |
| 9,711,056 | B1* | 7/2017 | Nguyen ............... A61B 5/165 |
| 2002/0097235 | A1* | 7/2002 | Rosenberg ......... G06Q 30/0241 345/204 |
| 2006/0281543 | A1* | 12/2006 | Sutton .................. G07F 17/32 463/29 |
| 2007/0066916 | A1* | 3/2007 | Lemos .................. A61B 3/113 600/558 |
| 2010/0149073 | A1* | 6/2010 | Chaum ............. G02B 27/0093 345/8 |
| 2013/0281798 | A1 | 10/2013 | Rau et al. |
| 2014/0159862 | A1* | 6/2014 | Yang ................... A61B 5/1171 340/5.52 |
| 2015/0268721 | A1* | 9/2015 | Joo ................... G02B 27/0093 345/156 |
| 2015/0334808 | A1* | 11/2015 | Hack .................... A61M 21/00 315/297 |
| 2016/0035132 | A1 | 2/2016 | Shuster et al. |
| 2016/0077547 | A1* | 3/2016 | Aimone ................. G06F 3/012 345/8 |
| 2016/0093154 | A1* | 3/2016 | Bytnar ............... G07F 17/3218 463/25 |
| 2016/0228771 | A1 | 8/2016 | Watson |
| 2017/0007182 | A1 | 1/2017 | Samec et al. |
| 2017/0055900 | A1 | 3/2017 | Jain et al. |

OTHER PUBLICATIONS

Dekker, Andrew, "Please Biofeed the Zombies: Enhancing the Gameplay and Display of Horror Game Using Biofeedback," Situated Play, Proceedings of DiGRA 2007 Conference, https://s3.amazonaws.com/academia.edu.documents/6145526/073.pdf?AWSAccessKeyId=AKIAIWOWYYGZ2Y53UL3A&Expires=1509990052&Signature=%2BrWi2dtaELj1x9hFOOU3VYYVMYk%3D&response-content-disposition=inline%3B%20filename%3DPlease_biofeed_the_zombies_enhancing_the.pdf, 2007.

* cited by examiner

CONFIGURATION FOR ADJUSTING A USER EXPERIENCE BASED ON A BIOLOGICAL RESPONSE

BACKGROUND

1. Field

This disclosure generally relates to the field of user experiences. More particularly, the disclosure relates to adjustments to user experiences based on biological responses.

2. General Background

As technology continues to develop at a rapid pace, various systems have been developed to provide users with more realistic and entertaining user experiences. For example, augmented reality ("AR"), virtual reality ("VR") and Mixed Reality systems generally provide realistic images and/or video that attempt to provide the user with a realistic feel of being present within the user experience. Even though such systems provide an extra sense of realism to enhance the user's entertainment experience, use of such systems often involves a number of adverse effects, e.g., nausea, eyestrain, headaches, motion sickness, etc. As a result, users may reduce their usage time of these systems.

SUMMARY

In one aspect, an apparatus has a receiver that receives a biological response of a user to an event that occurs during a user experience. Further, the apparatus has a memory that stores one or more predefined criteria that indicate an expected biological response to the event. In addition, the apparatus has a processor that compares the biological response to the one or more predefined criteria and adjusts the user experience based at least upon the biological response failing to meet the one or more predefined criteria.

In another aspect, a computer program product comprises a non-transitory computer readable storage device having a computer readable program stored thereon. The computer readable program when executed on a computer causes the computer to receive, with a receiver, a biological response of a user to an event that occurs during a user experience. Further, the computer readable program when executed on the computer causes the computer to store, with a memory, one or more predefined criteria that indicate an expected biological response to the event. In addition, the computer readable program when executed on the computer causes the computer to compare, with a processor, the biological response to the one or more predefined criteria. The computer readable program when executed on the computer also causes the computer to adjust the user experience based at least upon the biological response failing to meet the one or more predefined criteria.

In yet another aspect, a process receives, with a receiver, a biological response of a user to an event that occurs during a user experience. Further, the process stores, with a memory, one or more predefined criteria that indicate an expected biological response to the event. In addition, the process compares, with a processor, the biological response to the one or more predefined criteria. The process also adjusts the user experience based at least upon the biological response failing to meet the one or more predefined criteria.

BRIEF DESCRIPTION OF THE DRAWINGS

The above-mentioned features of the present disclosure will become more apparent with reference to the following description taken in conjunction with the accompanying drawings, wherein like reference numerals denote like elements and in which.

DETAILED DESCRIPTION

A configuration for adjusting a user experience based on a biological response of a user to an event in that user experience is provided. Various user experiences may be intended to elicit quite different biological user responses from one another. For example, a VR video game may be intended to elicit excitement (a corresponding increased heart rate) whereas a theme park show may be intended to elicit relaxation (a corresponding decreased heart rate). The configuration detects a deviation of the user's particular biological response to an event in the user experience from the intended biological response and adjusts the user experience so that the user experience is able to elicit a biological response from the user that conforms with the intended biological response. For example, the configuration may detect that the VR video game has elicited an increased heart for the user that is outside a threshold for an acceptable health norm and may adjust the current scene in the VR video game to be less action packed so that the user's heart rate returns to being within the threshold for the acceptable norm. As another example, the configuration may detect that the VR video game has elicited a decreased heart rate (corresponding to boredom) even though the intended biological response was excitement. As a result, the configuration may adjust the VR video game to be more action packed so that the user's heart rate is increased to a level corresponding to excitement.

Figure 1:
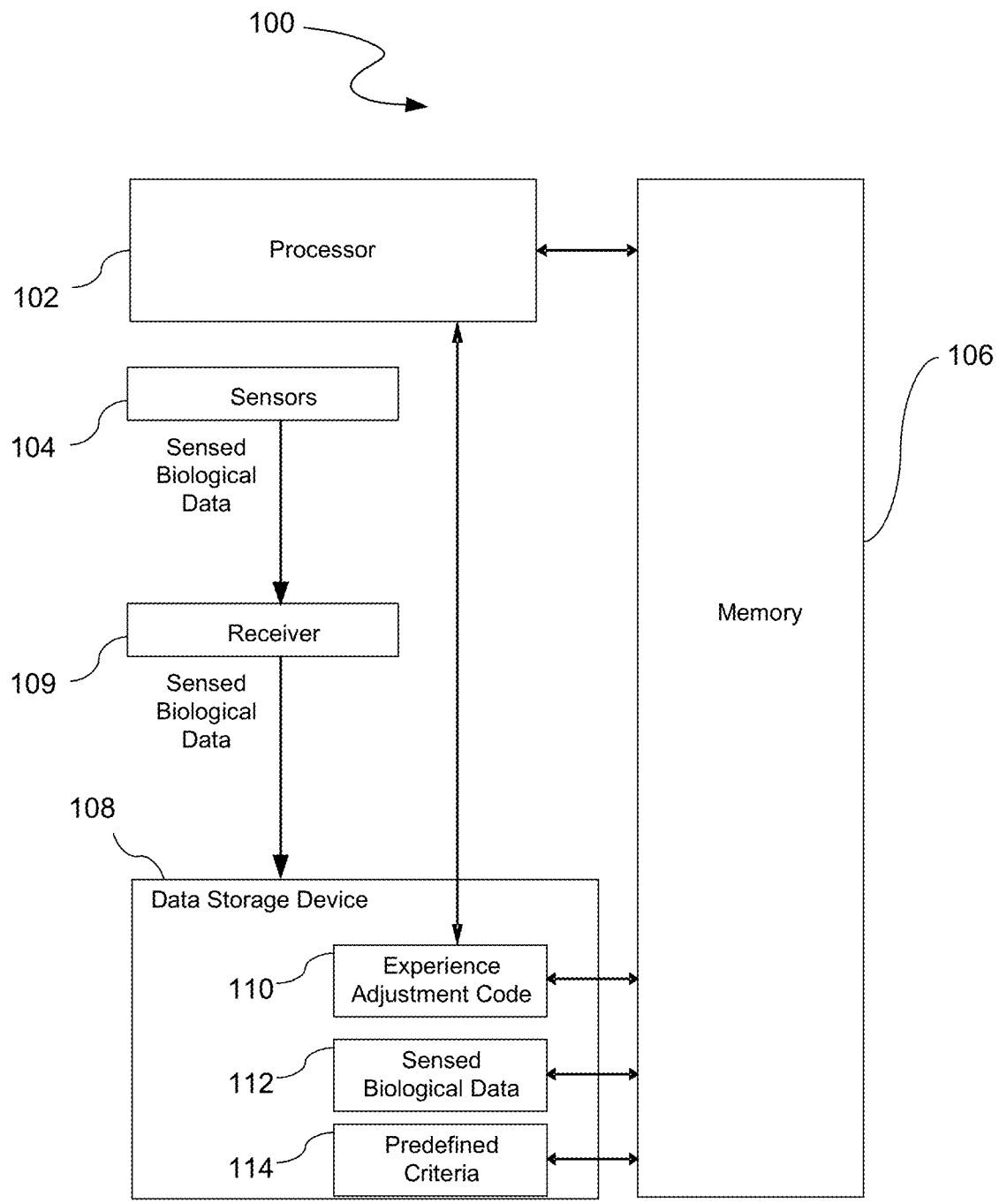
FIG. 1 illustrates an experience adjustment system that is used to adjust a user experience if an event in the user experience has elicited a biological response that deviates from the intended biological response corresponding to that user experience.

FIG. 1 illustrates an experience adjustment system 100 that is used to adjust a user experience if an event in the user experience has elicited a biological response that deviates from the intended biological response corresponding to that user experience. In one aspect, the experience adjustment system 100 is a user experience device that provides a user with a user experience. For example, the experience adjustment system 100 may be an AR headset, a VR headset, a television console, a gaming console, a theme park feature, etc.

As illustrated, the experience adjustment system 100 comprises a processor 102, a memory 106, e.g., random access memory ("RAM") and/or read only memory ("ROM"), a data storage device 108, and various sensors 104. The sensors 104 may sense various biological properties of one or more users that are participating in the user experience. Examples of the sensors 104 include cameras, biometric sensors, infrared ("IR") head sensors, smart watches, smart glasses, mobile devices, clothes, bracelets, fitness bands, necklaces, drones, and/or any other sensor that may automatically sense biological properties of the user without any manual input from the user. Examples of the sensed biological properties include pulse rate, blood pressure, temperature, pupil dilation, sweat, and galvanic skin response. The sensors 104 may store sensed biological data 112 corresponding to such properties, directly or indirectly, in the data storage device 108 and/or the memory 106.

In one aspect, the sensors 104 are integrated within the experience adjustment system 100. In another aspect, the sensors 104 are not integrated within the experience adjustment system 100 but are in operable communication with the experience adjustment system 100; such operable communication may be direct and/or indirect communication. For example, a sensor 104 may send data directly to the experience adjustment system 100 (e.g., the sensor 104 is in close proximity to the experience adjustment system 100), or data may be aggregated via a cloud service from the sensor 104 (e.g., a remote sensor 104) for retrieval by the experience adjustment system 100. For instance, a sensor 104 may send the sensed biological data to a receiver 109 of the experience adjustment system 100 that may or may not be remotely located from the sensor 104, or the sensor 104 may act as a receiver 109 that is integrated within the experience adjustment system 100.

Further, the data storage device 108 and/or the memory 106 may store predefined criteria 114. Examples of the predefined criteria 114 include various thresholds based upon biological measurements such as pulse rate, blood pressure, temperature, pupil dilation, sweat, brainwave patterns (e.g., via brainwave monitoring), physical disabilities, mental disabilities, color blindness, and/or galvanic skin response. The processor 102 compares the sensed biological data 112 with the predefined criteria 114 to determine if the user's biological response to an event within a user experience is in accord with the expected biological response for that particular event. Examples of expected biological responses include boredom, excitement, discomfort, and health risk. If the predefined criteria 114 are not met, the experience adjustment system 100 performs an adjustment to the user experience so that the user's biological response conforms to the expected biological response.

In one aspect, the data storage device 108 loads experience adjustment code 110 from a computer readable storage device, e.g., a magnetic or optical drive, diskette, or non-volatile memory, DVD, CD-ROM, etc. The experience adjustment code 110 is then operated by the processor 102 in the memory 106 of the experience adjustment system 100 to adjust the user experience if the processor 102 determines that the sensed biological data 112 does not meet the predefined criteria 114 (e.g., a predefined threshold, a standard biological norm, etc.). In another aspect, the data storage device 108 is the computer readable storage device. In yet another aspect, the experience adjustment code 110 is stored in the memory 106 rather than the data storage device 108. As such, the experience adjustment code 110 and associated data structures of the present disclosure may be stored on a computer readable storage device.

If the expected biological response is a comfort level that is not within an accepted health norm, the experience adjustment system 100 may reduce the possibility of a user's discomfort by sensing corresponding biological responses such as the following: motion sickness (dizziness, headaches, nausea, and disorientation), visual problems (double vision, blurred vision, focal difficulty), ocular problems (eye sore, eye pain, and pulled eye muscle), physical problems (neck aches and general discomfort), aural problems (ear pain, ear pressure, hearing loss, and ear ringing), and cognitive problems (difficulty thinking or concentrating). Accordingly, the experience adjustment system 100 extends the amount of time that the user participates in the user experience by reducing the discomfort of the user when the user is uncomfortable and by increasing the excitement of the user when the user is bored.

Further, the experience adjustment system 100 improves the functioning of a computing device by reducing the processing time to provide a customized user experience. In contrast with a manual calibration of a device that provides a user experience, the experience adjustment system 100 automatically senses data that may not even feasibly be determined through manual calibration. For example, the process of a user attempting to provide manual subjective inputs for comfort level is ostensibly more time-consuming than the processor 104 obtaining biotelemetry signals from the user and processing those signals to automatically determine whether or not to perform a user experience adjustment. In other words, the data model stored in the data storage device 108 and/or memory 106, e.g., the sensed biological data 112 and the predefined criteria 114, allows the processor 104 to have increased flexibility to adjust a user experience via data that the user may be unaware of. As a result, the functionality of a computer is improved by providing adjustments to user experiences during pertinent events that affect biological properties of the user, which may be unbeknownst to the user until after the user experiences an unintended effect.

Although the components of the experience adjustment system 100 are illustrated in FIG. 1 as being integrated within one device, the components may alternatively communicate with each other remotely through a network connection. For example, the processor 102 may be stored on a remote server that communicates with the sensors 104 stored in a wearable device worn by the user. Alternatively, the processor 102 may be built into a sensor 104 itself. For example, the processor 102 may be integrated into a sensor 104 of a wearable device (e.g., headset, watch, bracelet, glasses, etc.) or an adjoining apparatus of the wearable device. As yet another example, the processor 102 may be integrated into a wearable device, but the sensor 104 may be a distinct device that communicates, indirectly (through the receiver 109) or directly, with the processor 102. As another example, the sensor 104 may be built into a non-wearable device such as a camera that also has an integrated processor 102 (e.g., to measure pupil dilation and adjust the user experience accordingly).

Figure 2:
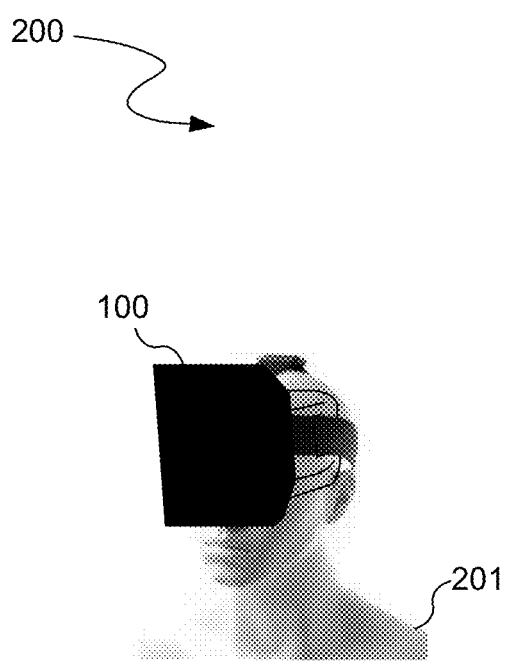
FIG. 2 illustrates an example of a device that provides a user experience.

FIG. 2 illustrates an example of a device that provides a user experience. A VR configuration 200 in which a user 201 uses a head mounted VR device 100 to view a VR environment is illustrated. The VR configuration 200 is provided only for illustrative purposes as a variety of other user experience environments (e.g., AR, VR, a motion picture, a video game, an audio recording, etc.) may be used instead.

Figure 3A:
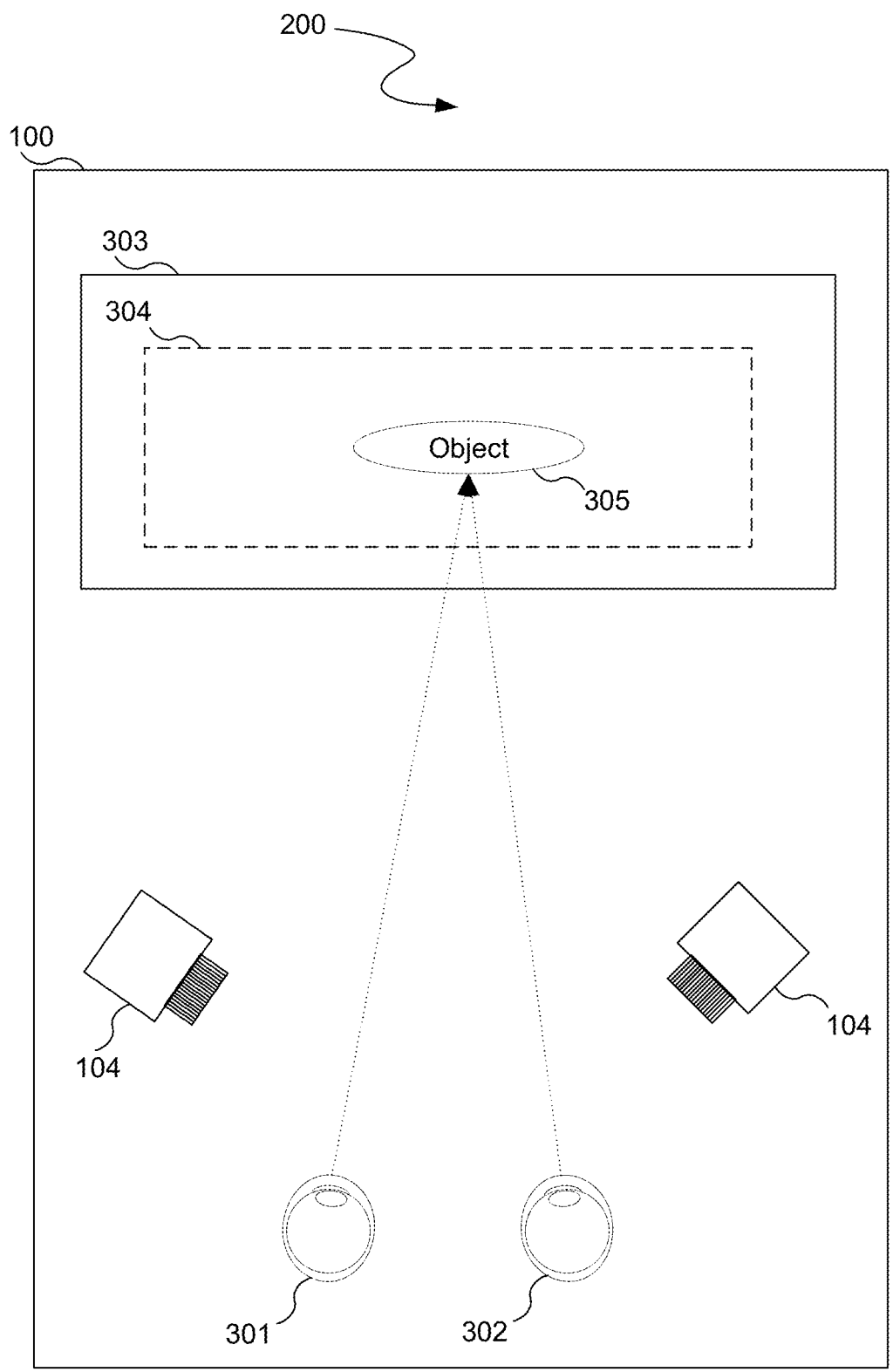
FIG. 3A illustrates a top view of the head mounted VR device illustrated in FIG. 2.

Further, FIG. 3A illustrates a top view of the head mounted VR device 100 illustrated in FIG. 2. Various cameras 104 are used to sense biological responses of the user 201 to events displayed on a display screen 303 in the head mounted VR device 100. For example, the cameras 104 are used to monitor a left eye 301 and a right eye 302 of the user 201 (FIG. 2) during the VR display on the display screen 303. The cameras 104 may be used to detect indications of eye strain (e.g., excessive blinking, swollen or dilated blood vessels, watery eyes, etc.).

For instance, the head mounted VR device 100 may not have detected any biological response from the user 201 (FIG. 2) to a scene 304 until introduction of an object 305. The left eye 301 and the right eye 302 converged on the object 305, and the cameras 104 detected eye strain that exceeded the predefined criteria 114 (FIG. 1) of what is deemed acceptable eye strain. As a result, the processor 102 (FIG. 1), which is either positioned within the head mounted VR device 100 or is in remote communication with the head mounted VR device 100 via a network connection, performs an adjustment to the user experience in the VR environment.

Figure 3B:
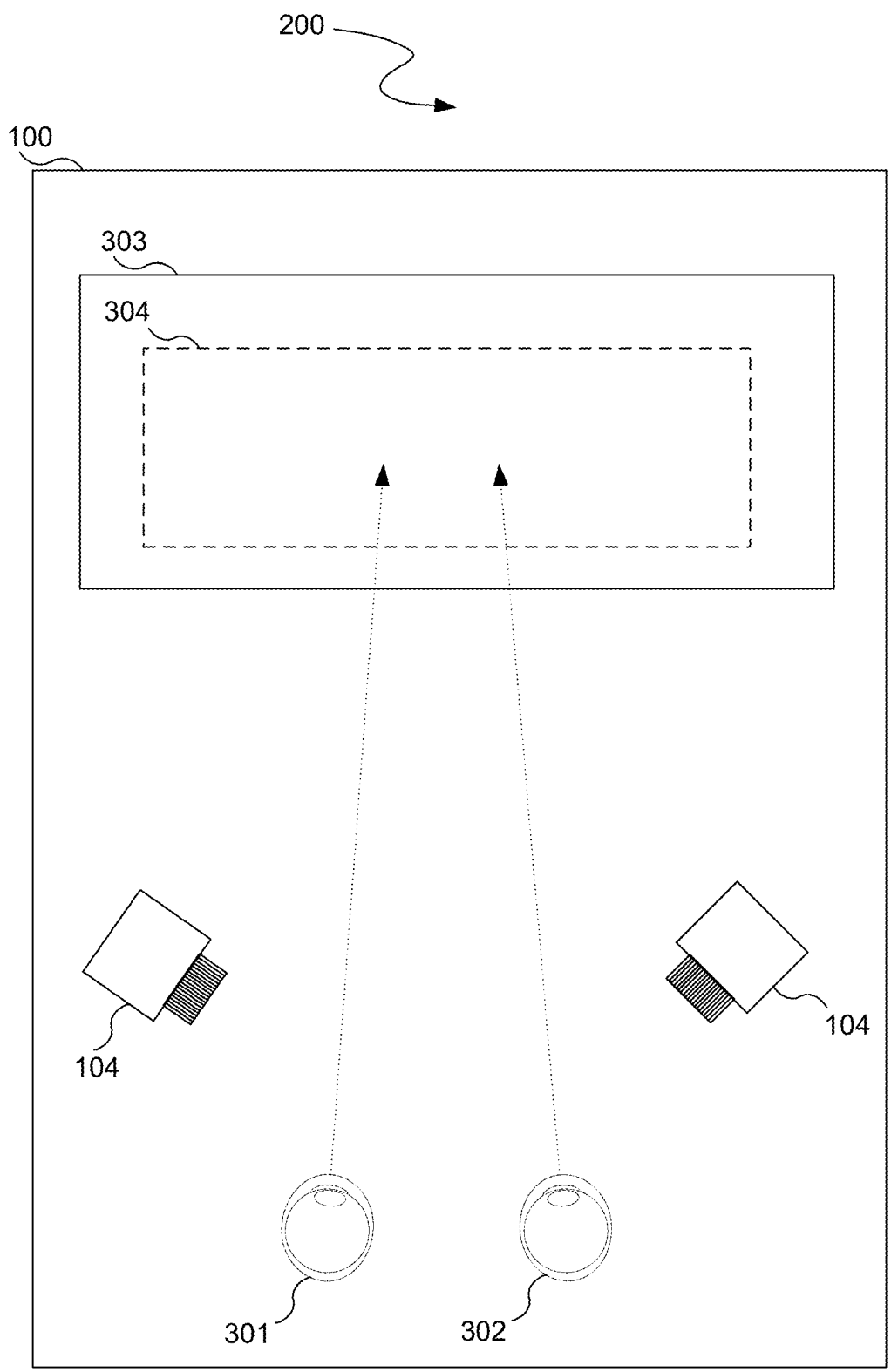
FIG. 3B illustrates an example of an adjustment to the user experience illustrated in FIG. 3A.

FIG. 3B illustrates an example of an adjustment to the user experience illustrated in FIG. 3A. Given that the introduction of the object 305 into the scene 304 resulted in a biological response that failed to meet the predefined criteria 114 (FIG. 1), the processor 102 (FIG. 1) adjusted the user experience by deleting the object 305 from the scene 304. As illustrated in FIG. 3B, the left eye 301 and the right eye 302 diverged to resume viewing of the scene 304 and return to a state in which eye strain is mitigated (e.g., reduced eye soreness, dryness, etc.). Alternatively, the processor 102 may have deleted the scene 304 in its entirety from the scene layout of the VR content, modified properties of the object 305 (e.g., color, brightness, contrast, etc.), and/or performed various other changes to the content and/or delivery of the content of the VR user experience to reduce the discomfort of the user 201 (FIG. 2). For example, the processor 102 may also modify properties of the entire scene (e.g., dynamic range from high dynamic range ("HDR") to standard dynamic range ("SDR"), visual depth change, parallax change, frame rate change, audio volume change, etc.). The processor 102 may also modify properties associated with an apparatus that is in contact with the user 201, e.g., a haptic signal provided to a wearable device worn by the user 201.

As yet another alternative, the processor 102 (FIG. 1) may pause the user experience and provide an interim user experience until the biological response meets the predefined criteria 114 (FIG. 1). For example, the processor 102 may provide a cool-down period in which the processor 102 plays a soothing video until the left eye 301 and the right eye 302 return to a state in which eye strain is mitigated; subsequently, the processor 102 resumes play of the scene 304 with the object 305. In other words, the processor 102 may provide a dynamic cool-down period based on the biometrics of the user 201 (FIG. 2) returning to an acceptable excited stated for that user 201. Alternatively, the processor 102 may provide a fixed cool-down period by pausing the user experience for a predefined time period, e.g., two minutes, and resuming play of the scene 304 with the object 305 irrespective of the current biological response of the user 201. For example, when the experience adjustment system 100 (FIG. 1) senses that the user 201 does not feel motion sickness anymore, that the heart rate of the user 201 returns to normal, or that the eyes of the user 201 have recovered, the experience adjustment system 100 returns the user 201 back to the game at the place where the user 201 left off, or thirty seconds before the user 201 left off. The following is an example of the biometric/emotional mood transitions: bored→excited→discomfort→health risk→discomfort→back to excited. In other words, the experience adjustment system 100 attempts to bring the user 201 back to an excited state.

In one aspect, the processor 102 (FIG. 1) automatically determines an adjustment to the user experience. In another aspect, the processor 102 receives an input from the user 201 (FIG. 2) via a menu selection of an option for the particular adjustment to the user experience preferred by the user 201.

The VR example provided in FIGS. 3A and 3B is provided only for illustrative purposes and is not intended to be exhaustive as the configurations provided for herein may be used in a variety of other user experience contexts and may adjust a variety of other types of content and/or content delivery features. For instance, the configuration for adjusting a user experience based on a biological response may be used with AR glasses to automatically adjust the content delivery, e.g., brightness, contrast, etc., of content displayed by the lenses of the AR glasses.

The configuration for adjusting a user experience based on a biological response may also be used without any type of headset. For example, a user may be watching a motion picture or playing a video game via a media console. Various sensors 104 (FIG. 1), e.g., cameras, may be integrated within the media console or in operable communication with the media console to monitor the biological response of the user 201 (FIG. 2) to an event presented by the media console, e.g., via video, audio, etc. Alternatively, various wearable sensors 104 may be worn by the user 201 to provide biological response data to the media console so that the media console may adjust the user experience.

Further, the configuration for adjusting a user experience based on a biological response may also be used in a theme park feature or a theater environment. For example, the processor 102 (FIG. 1) may detect an unacceptable increase in blood pressure from a participant of a theme park ride and may reduce the speed of the theme park ride until the blood pressure of the participant resumes at an acceptable level.

The predefined criteria 114 (FIG. 1) that is used by the processor 102 (FIG. 1) as a basis for comparison with the biological response for the user 201 (FIG. 2) may be defined prior to or during receipt of the biological response of the user. In one aspect, the predefined criteria 114 (FIG. 1) are based on baseline data associated with previous biological response from users gathered over a previous period of time (e.g., statistics of the biological responses of previous users) in a manner that is not real-time.

Figure 4:
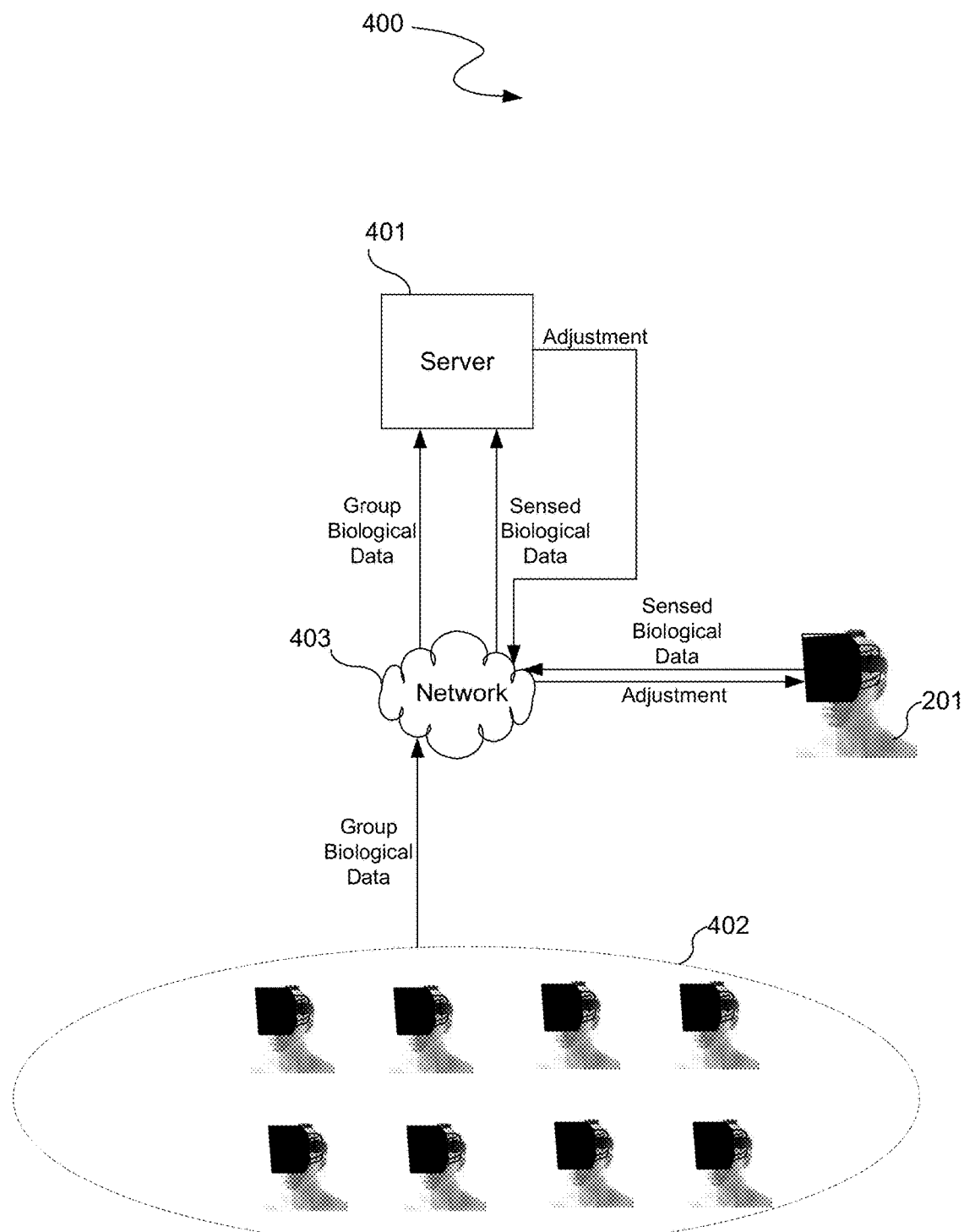
FIG. 4 illustrates a server configuration in which a server communicates with the user and a group of additional users during a user experience.

In another aspect, the predefined criteria 114 are based on real-time biological response data of other users that are concurrently participating in the same user experience as the user 201 (FIG. 2). FIG. 4 illustrates a server configuration 400 in which a server 401 communicates with the user 201 and a group of additional users 402 during a user experience. The server 401 receives group biological data, i.e., a set of biological responses to the same event during a user experience, from the group of additional users 402 through a network 403. Further, the server 401 then establishes baseline data based on that group biological data. As an example, the server 401 may determine a mean biological response and various standard deviations. The server 401 may also receive the sensed biological data 112 (FIG. 1) from the user 201.

In one aspect, the server 401 receives the group biological data and the sensed biological data 112 (FIG. 1) concurrently when the event for the user experience is being presented to the user 201 and the group of additional users 402 in a simultaneous or substantially simultaneous manner. In another aspect, the server 401 may update the group biological data and/or the sensed biological data 112 when a biological response is received during the user experience. For example, different sensors 104 (FIG. 1) may send the server 401 data at different times. Further, the event may occur at different times during the same user experience for different users.

Instead of the processor 102 (FIG. 1) being positioned in each user device, e.g., each head mounted VR device 100, the processor 102 may be positioned at the server 401 so that the server 401 may determine if the user experience is to be adjusted. For instance, the server 401 may compare the sensed biological data 112 (FIG. 1) with the group biological data, i.e., the baseline data, to determine if the sensed biological data 112 is within a predetermined threshold, e.g., within one standard deviation of the mean biological response. If the sensed biological data 112 does not meet the predetermined threshold, the server 401 may send an adjustment of the user experience only to the user 201.

Alternatively, the server 401 may include the sensed biological data 112 in the entire group biological data. The server 401 may then adjust the user experience for all of the users, i.e., the user 201 and the group of users 402, based upon any user's biological response deviating from the predetermined threshold.

As yet another alternative, the predefined criteria may be defined solely with respect to the user 201 without any analysis of the biological responses of other users. For example, the processor 102 (FIG. 1) may provide the user with a calibration test (e.g., a game, an eye tracking pattern for the user to follow, etc.) that determines the typical biological response for the user 201 (FIG. 2). The processor 102 (FIG. 1) may then compare the sensed biological data 112 with the typical biological response for the user 201 to determine if the sensed biological data 112 exceeds the predetermined threshold, e.g., one standard deviation from the mean biological response of the user 201, and then perform an adjustment to the user experience of the user 201.

Alternatively, the predefined criteria may be based on a combination of any of the foregoing baseline data compilations. For instance, the predefined criteria may be based on a combination of the baseline data of the user 201 gathered through a calibration test and the baseline data of the group of additional users 402 (FIG. 4), e.g., the group biological data. As an example, the server 401 may determine that the sensed biological data 112 (FIG. 1) is approximately the mean biological response of the user 201 but exceeds one standard deviation from the mean biological response of the group of additional users 402. The server 401 may be programmed to allow the user 201 to proceed with the event of the user experience given that the particular sensed biological data 112 indicates that the user 201 is comfortable during the event even though the group of additional users 402 may not have that comfort level. This example is not exhaustive as the server 401 may be programmed to dismiss one set of data in favor of another, consider all of the data sets but with different weightings, or a variety of other combinations.

In one aspect, the processor 102 (FIG. 1) generates a user profile for the user 201 (FIG. 2) based on adjustments to various user experiences and stores the user profile in the data storage device 108 (FIG. 1) and/or the memory 106 (FIG. 1). The processor 102 is then able to use that profile to preemptively adjust future user experiences for the user 201 prior to the user 201 experiencing an event. For example, the processor 102 may have previously determined that certain action events in video games have led to an unacceptable increased heart rate for a particular user 201. Rather than waiting for indications of another heart rate increase during a video game, the processor 102 may preemptively adjust any similar types of events in the current video game prior to the user viewing and/or listing to the event so that the user 201 does not have to undergo any discomfort.

Figure 5:
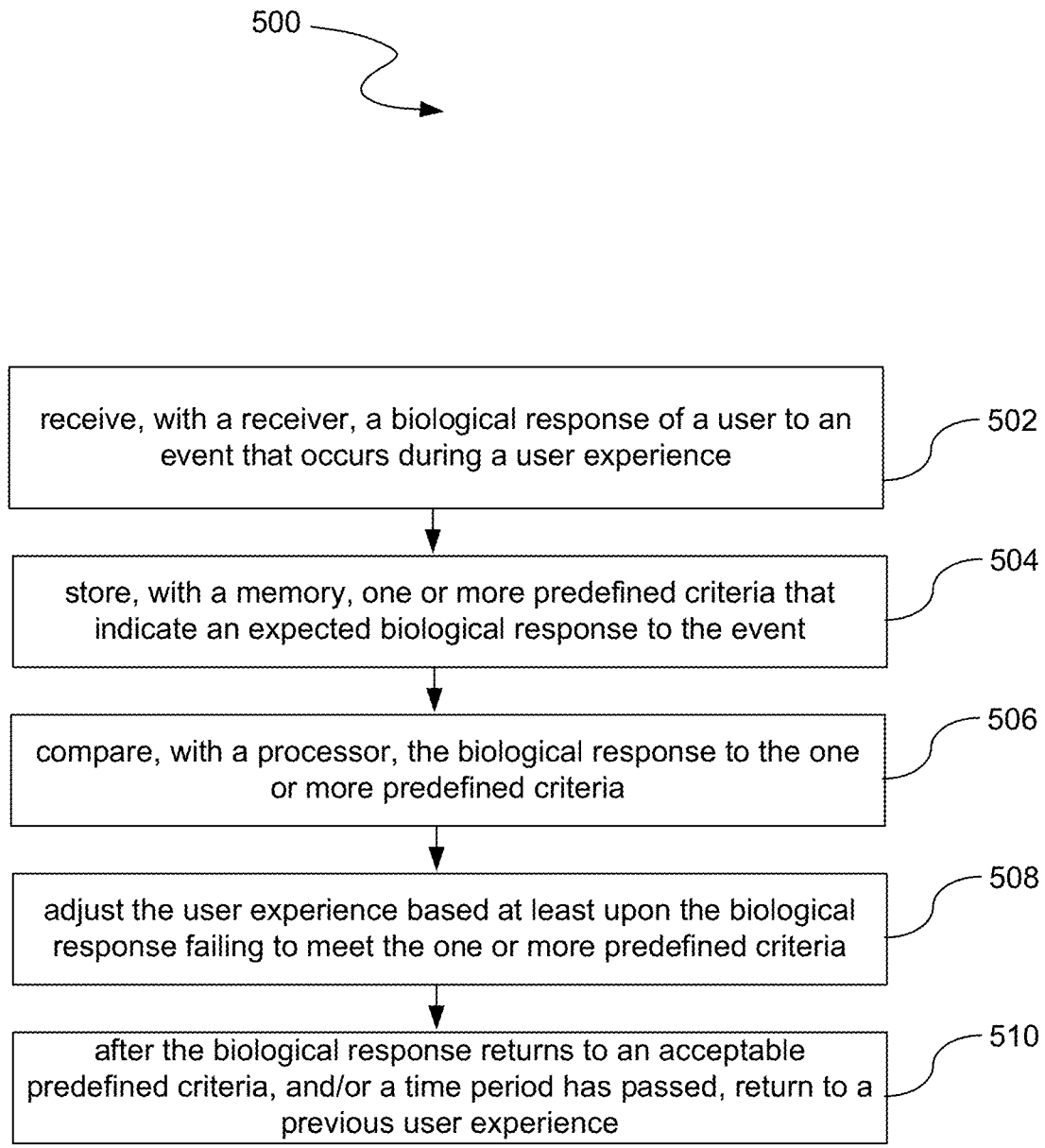
FIG. 5 illustrates a process that is used for the experience adjustment system illustrated in FIG. 1 to adjust a user experience.

Various processes may be used to adjust a user experience based on a biological response. FIG. 5 illustrates a process 500 that is used for the experience adjustment system 100 illustrated in FIG. 1 to adjust a user experience. At a process block 502, the process 500 receives, with the receiver 109 (FIG. 1), a biological response of the user 201 (FIG. 2) to an event that occurs during a user experience. Further, at a process block 504, the process 500 stores, with a memory 106 (FIG. 1), one or more predefined criteria 114 (FIG. 1) that indicate an expected biological response to the event. In addition, at a process block 506, the process 500 compares, with the processor 102, the biological response to the one or more predefined criteria 114. At a process block 508, the process 500 adjusts the user experience based at least upon the biological response failing to meet the one or more predefined criteria 114. In addition, at a process block 510, the process 500 returns to a previous user experience after the biological response returns to an acceptable predefined criteria and/or a time period has passed.

The processes described herein may be implemented in a specialized, general, multi-purpose, or single purpose processor. Such a processor will execute instructions, either at the assembly, compiled or machine-level, to perform the processes. Those instructions can be written by one of ordinary skill in the art following the description of the figures corresponding to the processes and stored or transmitted on a computer readable medium. The instructions may also be created using source code or any other known computer-aided design tool. A computer readable medium may be any medium, e.g., computer readable storage device, capable of carrying those instructions and include a CD-ROM, DVD, magnetic or other optical disc, tape, silicon memory (e.g., removable, non-removable, volatile or non-volatile), packetized or non-packetized data through wireline or wireless transmissions locally or remotely through a network. A computer is herein intended to include any device that has a specialized, general, multi-purpose, or single purpose processor as described above. For example, a computer may be a desktop computer, laptop, smartphone, tablet device, set top box, etc.

It is understood that the apparatuses, systems, computer program products, and processes described herein may also be applied in other types of apparatuses, systems, computer program products, and processes. Those skilled in the art will appreciate that the various adaptations and modifications of the aspects of the apparatuses, systems, computer program products, and processes described herein may be configured without departing from the scope and spirit of the present apparatuses, systems, computer program products, and processes. Therefore, it is to be understood that, within the scope of the appended claims, the present apparatuses, systems, computer program products, and processes may be practiced other than as specifically described herein.

We claim:

1. A virtual reality apparatus comprising:
a receiver that receives a biological response of a user to an event that occurs during a virtual reality user experience rendered by the virtual reality apparatus, the receiver being positioned within the virtual reality apparatus;
a memory that stores one or more predefined criteria that indicate an expected biological response to the event, the memory being positioned within the virtual reality apparatus, the expected biological response being based on baseline data that indicate a baseline response for a group of users to the virtual reality user experience; and a processor that compares the biological response to the one or more predefined criteria and adjusts the virtual reality user experience based at least upon the biological response failing to meet the one or more predefined criteria, the processor being positioned within the virtual reality apparatus.

2. The virtual reality apparatus of claim 1, wherein the expected biological response is selected from the group consisting of: boredom, excitement, discomfort, and health risk.

3. The virtual reality apparatus of claim 1, wherein the one or more predefined criteria comprise a threshold based upon a biological measurement selected from the group consisting of: pulse rate, blood pressure, body temperature, pupil dilation, sweat, brainwave patterns, physical response rate, and galvanic skin response.

4. The virtual reality apparatus of claim 1, wherein the processor adjusts the virtual reality user experience by adjusting a multimedia content feature selected from the group consisting of: a scene layout, a scene object, a scene color, and scene audio.

5. The virtual reality apparatus of claim 1, wherein the processor adjusts the virtual reality user experience by adjusting a multimedia delivery feature selected from the group consisting of: brightness, contrast, dynamic range, visual depth, parallax, frame rate, game difficulty level, and audio volume.

6. The virtual reality headset apparatus of claim 1, wherein the processor adjusts the virtual reality user experience by adjusting a haptic signal provided to an apparatus that is in contact with the user.

7. The virtual reality apparatus of claim 1, wherein the processor further adjusts the virtual reality user experience based on the biological response deviating from the baseline response.

8. The virtual reality apparatus of claim 1, wherein the processor receives the baseline data from a server that receives additional biological responses to the event from the group of users.

9. The virtual reality apparatus of claim 8, wherein the processor is integrated within a server that adjusts the virtual reality user experience and a plurality of additional user experiences based on the biological response of the user and one or more additional biological responses from users in the group of users deviating from the baseline response.

10. The virtual reality apparatus of claim 1, wherein the processor further adjusts the virtual reality user experience based on a manual input that indicates an additional biological response of the user.

11. The virtual reality apparatus of claim 1, wherein the processor further provides the user with a test, receives one or more biological test responses to the test from the user, and calibrates the one or more predefined criteria based on the one or more biological test responses to the test.

12. The virtual reality apparatus of claim 1, wherein the processor further generates a plurality of options, displays the plurality of options via a menu on a display device to the user, receives a menu selection, and performs the adjustment to the virtual reality user experience based on the menu selection.

13. The virtual reality apparatus of claim 1, wherein the processor adjusts the virtual reality user experience by pausing the virtual reality user experience, provides an interim user experience until the biological response meets the one or more predefined criteria, and subsequently resumes the virtual reality user experience.

14. The virtual reality apparatus of claim 1, wherein the processor adjusts the virtual reality user experience by pausing the virtual reality user experience, provides an interim user experience for a predetermined time period, and subsequently resumes the virtual reality user experience.

15. The virtual reality apparatus of claim 1, wherein the biological response is detected by a sensor, the sensor being selected from the group consisting of: a camera, a biometric sensor, and an infrared heat sensor.

16. A computer program product comprising a non-transitory computer readable storage device having a computer readable program stored thereon, wherein the computer readable program when executed on a computer causes the computer to:

receive, with a receiver at a virtual reality apparatus, a biological response of a user to an event that occurs during a virtual reality user experience rendered by the virtual reality apparatus;

store, with a memory at the virtual reality apparatus, one or more predefined criteria that indicate an expected biological response to the event, the expected biological response being based on baseline data that indicate a baseline response for a group of users to the virtual reality user experience;

compare, with a processor at the virtual reality apparatus, the biological response to the one or more predefined criteria; and adjust the virtual reality user experience based at least upon the biological response failing to meet the one or more predefined criteria.

17. A method comprising:

receiving, with a receiver at a virtual reality headset apparatus, a biological response of a user to an event that occurs during a virtual reality user experience rendered internally by the virtual reality headset apparatus;

storing, with a memory at the virtual reality headset apparatus, one or more predefined criteria that indicate an expected biological response to the event, the expected biological response being based on baseline data that indicate a baseline response for a group of users to the virtual reality user experience;

comparing, with a processor at the virtual reality headset apparatus, the biological response to the one or more predefined criteria; and adjusting the virtual reality user experience, as rendered internally by the virtual reality headset apparatus, based at least upon the biological response failing to meet the one or more predefined criteria.

* * * * *